United States Patent [19]

Biggs et al.

[11] Patent Number: 5,516,870
[45] Date of Patent: May 14, 1996

[54] METHODS OF MAKING POLYSILOXANES

[75] Inventors: Timothy N. Biggs; Gary E. Le Grow, both of Midland, Mich.

[73] Assignee: Dow Corning Corporation, Midland, Mich.

[21] Appl. No.: 433,181

[22] Filed: May 3, 1995

[51] Int. Cl.$^6$ .................................................... C08G 77/08
[52] U.S. Cl. ............................ 528/15; 556/460; 556/479
[58] Field of Search ................................. 556/460, 479; 528/15

[56] References Cited

U.S. PATENT DOCUMENTS

| | | |
|---|---|---|
| 2,469,890 | 5/1949 | Patnode . |
| 2,491,843 | 12/1949 | Wilcock . |
| 2,823,218 | 2/1958 | Speier . |
| 3,484,468 | 12/1969 | Curry ........................................ 556/460 |
| 4,160,775 | 7/1979 | Schilling, Jr. ............................ 556/460 |
| 5,017,221 | 5/1991 | Le Grow .................................... 106/2 |
| 5,359,113 | 10/1994 | Bank ......................................... 556/479 |
| 5,395,956 | 3/1995 | Haines ...................................... 556/451 |

OTHER PUBLICATIONS

European Polymer Journal, vol. 29 No. 1, pp. 15–22, (1993).

*Primary Examiner*—Melvyn I. Marquis
*Attorney, Agent, or Firm*—James L. DeCesare

[57] ABSTRACT

Linear or straight-chain trimethylsiloxy endcapped methylhydrogen polysiloxanes are made by contacting hexamethyldisiloxane with a highly pure methylhydrogen cyclic siloxane, in the presence of anhydrous trifluoromethane sulfonic acid catalyst at room temperature. Trimethylsiloxy endcapped alkylmethyl siloxanes are made by reacting the linear or straight-chain trimethylsiloxy endcapped methylhydrogen polysiloxanes with an alpha-olefin, in the presence of a platinum catalyst. Alkylmethyl cyclic siloxanes containing zero parts per million residual ≡SiH, are made by reacting anhydrous alpha-olefins and a highly pure methylhydrogen cyclic siloxane, in the presence of dried platinum supported on carbon catalyst.

4 Claims, No Drawings

METHODS OF MAKING POLYSILOXANES

BACKGROUND OF THE INVENTION

This invention is directed to methods for preparing linear or straight-chain, and cyclic polysiloxanes.

Acid equilibration (polgerization) of siloxanes such as tetramethyl cyclotetrasiloxane ($D^H4$) and pentamethyl cyclopentasiloxane ($D^H5$) has been performed in the past, but the method of our invention relates to the polymerization of highly pure silanol-free hexamethyldisiloxane and highly pure mixtures of silanol-free $D^H4$ and $D^H5$ containing no more than about 100 parts per million (ppm) water, with anhydrous trifluoromethane sulfonic acid (triflic acid, $CF_3SO_3H$), at room temperature, to provide access to linear or straight-chain methylhydrogen siloxanes of molecular weight up to about $MD^H_{2200}M$.

Hydrosilation ($\equiv SiH+CH_2=CHR=SiCH_2CH_2R$) of alpha-olefins with methylhydrogen siloxanes has been performed in the past, but the method of our invention relates to hydrosilation of alpha-olefins with high molecular weight methylhydrogen siloxanes (degree of polymerization up to about 2200), efficiently performed to provide alkylmethyl polysiloxanes with low $\equiv SiH$ content.

Cyclosiloxanes have been alkylated in the past but afford products with substantial levels of residual refill. The method of our invention relates to the use of highly pure silanol-free tetramethylcyclotetrasiloxane $(CH_3HSiO)_4$ and highly pure silanol-free pentamethylcyclopentasiloxane $(CH_3HSiO)_5$ containing no more than about 100 ppm water, that are 100% alkylated, leaving no detectable residual $\equiv SiH$, using anhydrous alpha-olefins ranging from ethylene gas to C30+ alkenes in the presence of a dried anhydrous platinum supported on carbon catalyst.

It is known that methylhydrogen chlorosilanes can be hydrolyzed and condensed to obtain silicone fluids retaining a high proportion of reactive hydrogen, but typically they contain 1% or more of branch sites. The reactions are often difficult to control, and the results are erratic (i) sometimes producing useless gels or hard brittle solids instead of fluids, and (ii) hydroxyl substitution on silicon ($\equiv SiOH$) which leads to gelation. This limits the usefulness of methylhydrogen siloxanes as starting materials for polymer synthesis.

These disadvantages have been overcome in our invention by utilizing highly pure essentially anhydrous silanol-free organodisiloxanes, and highly pure essentially anhydrous silanol-free methylhydrogen cyclic siloxanes ($D^H4$) and ($D^H5$), as starting materials.

Since our starting materials contain no water or residual $\equiv SiOH$, branching and cross-linking do not occur. Therefore, our end products are not branched-chain polysiloxanes or gels, but linear or straight-chain polysiloxanes. The interested reader is referred to U.S. Pat. No. 2,469,890 (May 10, 1949) for illustrations showing the structural differences between linear or straight-chain and branched-chain polysiloxanes.

Our invention, therefore, is in sharp contrast to the gel containing cross-linked oily materials taught in U.S. Pat. No. 2,491,843 (Dec. 20, 1949); or the cross-linked high polymers bearing SiOH end groups, described in the European Polymer Journal, Vol. 29, No. 1, Pages 15–22, (1993). Furthermore, our alkylated products are prepared from highly pure essentially anhydrous silanol-free starting materials and contain low or no residual $\equiv SiH$.

SUMMARY OF THE INVENTION

It is an object of the invention to provide a method of making trimethylsiloxy endcapped methylhydrogen polysiloxanes at room temperature, by forming a reaction mixture containing a pure organodisiloxane and a pure methylhydrogen cyclic siloxane, contacting the mixture with anhydrous trifluoromethane sulfonic acid catalyst, and agitating the mixture and the catalyst until a trimethylsiloxy endcapped methylhydrogen polysiloxane is produced with substantially reduced branching sites.

It is another object of the invention to provide a method of making trimethylsiloxy endcapped alkylmethyl siloxanes, by contacting and reacting the trimethylsiloxy endcapped methylhydrogen polysiloxane formed according to our first object, with an alpha-olefin in the presence of a platinum catalyst.

It is a further object of the invention to provide a method of making alkylmethyl cyclic siloxanes, by forming a reaction mixture of an anhydrous alpha-olefin and a pure methylhydrogen cyclic siloxane, contacting the mixture with dried anhydrous platinum supported on carbon catalyst, and agitating the mixture and catalyst until an alkylmethyl cyclic siloxane with zero ppm residual $\equiv SiH$ is formed.

These and other objects of the invention will become apparent from a consideration of the detailed description.

DETAILED DESCRIPTION OF THE INVENTION

According to the first embodiment of our invention, high molecular weight trimethylsiloxy-endcapped methylhydrogen siloxanes are prepared via an anhydrous triflic acid catalyzed, mild room temperature polymerization, of highly pure essentially anhydrous silanol-free hexamethyldisiloxane $(CH_3)_3SiOSi(CH_3)_3$, highly pure essentially anhydrous silanol-free tetramethylcyclotetrasiloxane, and highly pure essentially anhydrous silanol-free pentamethylcycleopentasiloxane.

By silanol-free is meant that the siloxane starting materials contain no residual $\equiv SiOH$, within the limits of detection by Silicon-29 Nuclear Magnetic Resonance ($^{29}Si$ NMR) and Fourier Transform Infrared Spectroscopy (FTIR), which is one part per million or less. The resulting linear or straight-chain trimethylsiloxy-endcapped methylhydrogen siloxanes are fluids containing less than 0.2% branch sites by 29Si NMR, that could eventuate in the formation of an undesirable gel. A branch site frequency of 0.2% means that 1 out of 500 silicon atoms contains a branch site. Reaction conditions are mild so that branch sites are not formed during polymerization. Thus, the preferred temperature range is about 20°–30° C. (68°–86° F.), although if desired, temperatures up to about 100° C. can be employed, consonant with the desire to avoid the formation of branch sites.

The method of preparing these high molecular weight trimethylsiloxy-endcapped methylhydrogen siloxanes is illustrated in the following examples.

EXAMPLE I

Preparation of $(CH_3)_3Si$ $(CH_3HSiO)_{758}Si$ $(CH_3)_3$ or $MD^H_{758}M$

A solution of silanol-free hexamethyldisiloxane (0.05 g, 0.31 mmol), a silanol-free mixture of 50% by weight $D^H4$ and 50% by weight $D^H5$ (57.6 g, 0.213 mol), and 0.1% by weight anhydrous triflic acid, containing less than about 100 ppm water determined by FTIR, was stirred for one hour at room temperature (20°–25° C./68°–77° F.), then neutralized with $NaHCO_3$ (4 g). After neutralization of the reaction mixture, positive-pressure filtration provided a viscous oil.

Analysis of the unstripped product by 29Si NMR showed a degree of polymerization of 758. The room temperature stability of the product without gel formation exceeded two months. The product contained no branch sites.

EXAMPLE II

Preparation of $(CH_3)_3Si(CH_3HSiO)_{2156}Si(CH_3)_3$ or $MD^H{}_{2156}M$

A solution of silanol-free hexamethyldisiloxane (0.06 g, 0.37 mmol), a silanol-free mixture of 50% by weight $D^H4$ and 50% by weight $D^H5$ (80 g, 0.296 mol), and 0.05% by weight anhydrous triflic acid, containing less than about 100 ppm water, was stirred for 1.5 hours at room temperature, then neutralized with $NaHCO_3$ (5 g). After neutralization of the reaction mixture, positive-pressure filtration provided a viscous oil. Analysis of the unstripped oil by $^{29}Si$ NMR showed a degree of polymerization of 2156. The room temperature stability of the product without gel formation exceeded two months. The product contained 3 branch sites per average molecule which is a branch site frequency rate of 0.139%, i.e., (3/2156)(100).

Reaction mixtures may contain 0.001–1.0 mole of organodisiloxane per mole of methylhydrogen cyclic siloxane. The acid catalyst can be used in amounts of 0.05–0.2% by weight, based on the weight of the mixture. It can be neutralized with agents other than sodium bicarbonate, such as ammonia or calcium carbonate. The reaction is preferably conducted at room temperature. Reaction time will vary, depending upon equipment being used and amount of product being produced, but typically a batch reaction requires about 1–2 hours for completion.

The linear or straight chain trimethylsiloxy endcapped methyl hydrogen polysiloxane products are purified by filtration, although other standard means of separating end products from reaction mixtures can be employed, such as centrifugation. This method can be used to make linear or straight-chain trimethylsiloxy endcapped methylhydrogen polysiloxanes having a degree of polymerization of 1–2200, preferably 750–2200.

Silanol-free methyl hydrogen cyclicsiloxane starting materials containing less than about 100 ppm water can be made by processes such as described in U.S. Pat. No. 5,395,956 (Mar. 7, 1995), which is assigned to the assignee of this invention, and incorporated herein by reference. Briefly, according to that process, an organohydrogen dichlorosilane is contacted with about a stoichiometric equivalent of water to form a hydrolyzate. The hydrolyzate is diluted in an inert solvent, and contacted with an acid rearrangement catalyst to effect formation of cyclic organohydrogen siloxanes. The cyclic organohydrogen siloxanes are separated from the inert solvent and the linear organohydrogen siloxanes. The inert solvent and linear organohydrogen siloxanes are then recycled to the process for further contact with the acid rearrangement catalyst. According to that method, hydroxyl substitution on silicon is minimized.

$D^H4$, $D^H5$, and mixtures containing $D^H4$ and $D^H5$, are preferred methylhydrogen cyclic siloxanes according to our invention, but other methylhydrogen cyclic siloxanes such as $D^H6$ can also be used. In addition, the methylhydrogen cyclic siloxanes $(RHSiO)_n$ can be used alone or mixed with one another. Further, n can be 3–8, and alkyl group R may be other than methyl, such as ethyl, propyl, isopropyl, butyl, or hexyl.

Silanol-free hexaorganodisiloxanes $R_3Si-O-SiR_3$ containing less than about 100 ppm water, such as hexamethyldisiloxane are commercially available. Silanol-free disiloxanes where R is an alkyl group other than methyl, can also be employed. Thus, R can be another alkyl group such as ethyl, propyl, isopropyl, butyl, or hexyl. In addition, R can be an aryl group such as phenyl, xenyl, or naphthyl; an alkaryl group such as tolyl or xylyl; or an aralkyl group such as benzyl, phenylethyl, or 2-phenylpropyl.

According to the second embodiment of our invention, high molecular weight trimethylsiloxy-endcapped alkylmethylsiloxanes are prepared via hydrosilation of alpha-olefins, using the linear high molecular weight methylhydrogen siloxanes from Examples I and II. This scenario provides a route to alkylmethylsiloxanes containing less than 200 ppm hydrogen expressed as residual ≡SiH. Preferably, the alkylmethylsiloxanes contain 25–200 ppm, and most preferably 25–165 ppm hydrogen expressed as residual ≡SiH. This method is illustrated by the following examples.

EXAMPLE III

Preparation of Trimethylsiloxy-endcapped Polydecylmethylsiloxane $MD^{C10}{}_{758}M$ To a solution of 1-decene (80.9 g, 0.578 mol) and platinum (2.5 ppm, 16 rag, 2% Pt in toluene) was added via an addition funnel, 29 g/0.64 mmol $(CH_3)_3Si(CH_3HSiO)_{758}Si(CH_3)_3$ from Example I, over a period of four hours. After addition, the reaction was stirred at 110° C. for 12 hours. At this point, FTIR analysis showed 440 ppm ≡SiH. An additional 50 mL of 1-decene was added, and the reaction was continued at 110° C. for 6 hours. After excess olefin was stripped (2 mm Hg, 50°–100° C.) from the polymer, FTIR analysis showed 27 ppm ≡SiH.

EXAMPLE IV

Preparation of Trimethyl siloxy-endcapped Polydecylmethylsiloxane $MD^{C10}{}_{2150}M$ To a suspension of 1-decene (10.25 g, 0.073 mol, 1.1 eq.) and platinum supported on carbon (50 ppm, 14 mg), was added 4 g/0.03 mmol $(CH_3)_3Si(CH_3HSiO)_{2150}Si(CH_3)_3$ in hexane (25 mL), which provided a slight exotherm (70° C.). $MD^H{}_{2150}M$ was prepared according to the method of Example II. After stirring for 20 hours at 75° C., FTIR analysis of the reaction mixture showed 500 ppm ≡SiH. At this point, additional 1-decene (8.4 g, 0.059 mol) was added, and stirring was continued for 4 more hours at 75° C. After excess 1-decene was stripped (2 mm Hg, 50°–100° C.) from the product, FTIR analysis showed 165 ppm ≡SiH.

This method can be used to make linear or straight-chain trimethylsiloxy endcapped alkylmethyl siloxanes having a degree of polymerization of 1–2200, most preferably 750–2200, containing less than 200 ppm residual ≡SiH, most preferably 25–165 ppm residual ≡SiH.

According to the third embodiment of our invention, complete 100% alkylation of tetramethylcyclotetrasiloxane and pentamethylcyclopentasiloxane is achieved, using highly pure silanol-free cyclic siloxanes $D^H4$ and $D^H5$ containing less than about 100 ppm water, anhydrous alpha-olefins ($C_6$, $C_{18}$, and $C_{30+}$), and dried anhydrous platinum supported on carbon catalyst. The resulting alkylmethyl cyclic siloxanes contain no branch sites and are not gels. Complete consumption of ≡SiH in $D^H4$ and $D^H5$ has not been previously known, so this scenario provides a new method of making ≡SiH free alkylated cyclic siloxane fluids and waxes. By ≡SiH free and zero ppm residual ≡Si-H, is meant the amount of hydrogen present as ≡SiH, within the detection limits of Fourier Transform Infrared Spectroscopy (FTIR), which is less than one part per mi 11 ion.

The method of preparing $C_6$, $C_{18}$, and $C_{30+}$ substituted cyclotetrasiloxane and cyclopentasiloxane is illustrated in the following examples.

EXAMPLE V

Preparation of $(C_6H_{13}MeSiO)_{4.5}$

To a stirred suspension of dried anhydrous 5% platinum supported on carbon (105 mg, 50 ppm), and anhydrous 1-hexene (64.7 g, 0.77 mol) heated to reflux, was added a silanol-free mixture of 50% by weight $D^H4$ and 50% by weight $D^H5$ (40 g, 0.15 mol) containing less than 100 ppm water, at a drop-wise rate over a period of 1 hour. During addition of $D^H4$ and $D^H5$, the external heat source was removed, and an exotherm to 110° C. was observed. After addition of the cyclic siloxanes, the platinum catalyst was removed from the reaction mixture by vacuum filtration through a CELITE® pad, to afford a translucent oil. Within the detection limits of FTIR, analysis showed zero ppm hydrogen as residual $\equiv$Si-H.

EXAMPLE VI

Preparation of $(C_{18}H_{37}MeSiO)_{4.5}$

To a stirred suspension of dried anhydrous 5% platinum supported on carbon (63 mg, 50 ppm), and anhydrous 1-octadecene (54 g, 0.22 mol) heated to 120° C., was added a silanol-free mixture of 50% by weight $D^H4$ and 50% by weight $D^H5$ (10 g, 0.037 mol) containing less than 100 ppm water, at a drop-wise rate over a period of 30 minutes. After olefin addition, the mixture was stirred at 120° C. for 15 minutes. At this point, the platinum catalyst was removed from the reaction mixture by heated vacuum filtration through a CELITE® pad, to afford a white wax with a melting point of 35°–37° C. Within the detection limits of FTIR, analysis showed zero ppm hydrogen as residual $\equiv$Si-H.

EXAMPLE VII

Preparation of $(C_{30}H_{61}MeSiO)_{4.5}$

To a stirred suspension of dried anhydrous 5% platinum supported on carbon (34 mg, 50 ppm), and anhydrous C30+ alpha-olefin (28.3 g, 0.054 mol) heated to 110° C., was added a silanol-free mixture of 50% by weight $D^H4$ and 50% by weight $D^H5$ (2.9 g, 0.011 mol) containing less than 100 ppm water, at a drop-wise rate over a period of 30 minutes. After olefin addition, the mixture was stirred at 120° C. for 6 hours. At this point, the platinum catalyst was removed from the reaction mixture by heated vacuum filtration through a CELITE® pad, to afford a white wax with a melting point of 71°–73° C. Within the detection limits of FTIR, analysis showed zero ppm hydrogen as residual $\equiv$Si-H.

Alpha-olefins $CH_2\!\!=\!\!CHR$ useable in the methods in Examples III–VII include alkenes with 2–30+ carbon atoms, preferably 6–30 carbon atoms, and most preferably 6–18 carbon atoms. In Examples V–VII, particular care should be taken to insure that the alpha-olefin(s) is anhydrous.

Some suitable alpha-olefins are ethene, propene, 1-butene, isobutylene (2-methylpropene), 1-pentene (C5), 2-methyl- 1-butene, 3-methyl- 1-butene, 1-hexene, 2-methyl- 1-pentene, 3-methyl- 1-pentene, 4-methyl- 1-pentene, 1-heptene, 2-methyl-l-hexene, 1-octene, 2-methyl-l-heptene, 1-nonene, 1-decene (C10), 1-undecene, 1-dodecene, 1-tridecene, 1-tetradecene, 1-pentadecene (C15), 1-hexadecene, 1-octadecene, 1-nonadecene, 1-eicosene (C20), and those alpha-olefin fractions containing varying percentages of C22–C30+ alpha-olefins sold under the trademarks GULFTENE® 24–28 and GULFTENE®30+, by Chevron Chemical Company, Houston, Texas.

Equivalent amounts of $\equiv$Si-H containing reactants and unsaturated alpha-olefin reactants should be employed in the process, and one ethylenic linkage is the theoretical equivalent of one silicon bonded hydrogen atom. It may be necessary however to use an excess of alpha-olefin to totally consume $\equiv$SiH in the siloxane product.

The maximum amount of platinum catalyst employed is determined by economical considerations, and the minimum amount by the type and purity of reactants employed. Very low concentrations of platinum catalyst such as $1\times10^{-10}$ moles catalyst per equivalent of the alpha-olefin compound, may be used when the reactants are extremely pure. However, it is possible to use about $1\times10^{-8}$ moles catalyst per equivalent weight of alpha-olefin compound, and even $1\times10^{-7}$ to $1\times10^{-3}$ moles platinum catalyst, per equivalent weight of alpha-olefin.

"Moles" of platinum catalyst are measured in terms of one mole providing one unit atom (e.g., one gram atom) of platinum. An "equivalent weight" of alpha-olefin is the amount of reactant furnishing one unit weight of ethylenic unsaturation (i.e., equivalent to one unit weight of $\equiv$Si-H), regardless of what other reactive or potentially reactive substitutents may be present. Thus, an equivalent weight of ethylene is its molecular weight.

The preferred hydrosilation catalyst is platinum supported on active carbon particles having a diameter of 1–2 mm. The amount of platinum supported on the active carbon can vary from 0.1–5% by weight, based on the weight of active carbon. Care should be taken to insure that the platinum on carbon catalyst is dried so that it is anhydrous, in Examples V–VII.

The reaction temperature can vary, and optimum temperatures depend upon the concentration of platinum catalyst, and the nature of the reactants. The reaction can be initiated at a temperature below room temperature (0° to −10° C.), and is exothermic once begun. The temperature should be one at which both reactants are in a liquid or gaseous state. The maximum temperature is determined by the stability of the reactants. Ordinarily, it is best to keep the reaction temperature below about 300° C. Best results with most reactants are obtained by initiating the reaction at about 80° to 180° C., and maintaining the reaction within reasonable limits of this range. The exothermic nature of the reaction may push the temperature up to 200°–250° C. for a short time, however.

The optimum reaction time is a variable depending upon the reactants, reaction temperature, and platinum catalyst concentration. Ordinarily, there is no benefit in extending the contact time of the reactants beyond 16 or 17 hours, but likewise there is usually no harm, unless an extremely elevated temperature is employed. With many reactants, a practical quantitative yield of product can be obtained in 30 minutes or less.

The reaction can be carried out at atmospheric, sub-atmospheric, or super-atmospheric pressure. Here again, the choice of conditions is largely a matter of logic, based upon the nature of the reactants, and the equipment available. Non-volatile reactants are especially adaptable to being heated at atmospheric pressure, with or without a reflux arrangement. Reactants which are gaseous at ordinary temperatures, are preferably reacted at substantially constant volume under autogenous or induced pressure. The best results are obtained by maintaining all reactants in the liquid phase.

The linear trimethylsiloxy endcapped methylhydrogen polysiloxanes in Examples I and II are useful as intermediates for preparing linear trimethylsiloxy endcapped alkylmethyl siloxanes such as in Examples III and IV, which in turn, are useful in the personal care arena for conditioning skin, for instance. The alkylmethyl cyclic siloxanes in Examples V–VIII are also useful as skin conditioners.

Other variations and modifications may be made in the methods described without departing from the essential features of our invention. The forms of invention are exemplary and not limitations on the scope of the invention defined in the claims.

That which is claimed is:

1. A method of making alkylmethyl cyclic siloxanes comprising (i) forming a reaction mixture containing an alpha-olefin, one or more silanol-free methylhydrogen cyclic siloxanes, and less than about 100 parts per million water, (ii) contacting the essentially anhydrous silanol-free reaction mixture with anhydrous platinum supported on carbon catalyst, (iii) agitating the mixture and catalyst to form an alkylmethyl cyclic siloxane, and (iv) continuing the reaction until the alkylmethyl cyclic siloxane is ≡SiH free; SiH free being the amount of hydrogen present as SiH within the detection limits of Fourier Transform Infrared Spectroscopy or less than one part per million.

2. A method according to claim 1 in which the mixture contains tetramethyl cyclotetrasiloxane and pentamethylcyclopentasiloxane.

3. A method according to claim 1 in which the alpha-olefin is an alkene selected from the group consisting of ethene, propene, 1-butene, isobutylene (2-methylpropene), 1-pentene (C5), 2-methyl-1-butene, 3-methyl- 1-butene, 1-hexene, 2-methyl- 1-pentene, 3-methyl- 1-pentene, 4-methyl - 1-pentene, 1-heptene, 2-methyl- 1-hexene, 1-octene, 2-methyl-l-heptene, 1-nonene, 1-decene (C10), 1-undecene, 1-dodecene, 1-tridecene, 1-tetradecene, 1-pentadecene (C15), 1-hexadecene, 1-octadecene, 1-nonadecene, 1-eicosene (C20), and alpha-olefin fractions containing C22–C30+alpha-olefins.

4. An alkylmethyl cyclic siloxane prepared according to the method in claim 1.

* * * * *